(12) United States Patent
Gershon

(10) Patent No.: US 7,964,588 B2
(45) Date of Patent: Jun. 21, 2011

(54) METHOD FOR THE TREATMENT OF PSORIASIS

(75) Inventor: David Gershon, New York, NY (US)

(73) Assignee: Redox Phamaceutica Co., Inc., Greenvale, NY (US)

( * ) Notice: Subject to any disclaimer, the term of this patent is extended or adjusted under 35 U.S.C. 154(b) by 0 days.

(21) Appl. No.: 12/516,761

(22) PCT Filed: Oct. 23, 2007

(86) PCT No.: PCT/US2007/082227
§ 371 (c)(1),
(2), (4) Date: May 29, 2009

(87) PCT Pub. No.: WO2008/070317
PCT Pub. Date: Jun. 12, 2008

(65) Prior Publication Data
US 2010/0069487 A1 Mar. 18, 2010

Related U.S. Application Data

(60) Provisional application No. 60/867,679, filed on Nov. 29, 2006.

(51) Int. Cl.
*A61K 31/555* (2006.01)
(52) U.S. Cl. ........................................................ 514/185
(58) Field of Classification Search ................... 514/501, 514/836, 863
See application file for complete search history.

(56) References Cited

U.S. PATENT DOCUMENTS

| 4,822,605 A | 4/1989 | Powell |
| 2005/0032739 A1 | 2/2005 | Gershon |
| 2008/0063604 A1* | 3/2008 | Claudio ........................ 424/9.52 |

OTHER PUBLICATIONS

Nakanishi et al., Regulatory Role for Kruppel-Like Zinc-Finger Protein Gli0Similar 1 (Glis1) in PMA-Treated and Psoriatic Epidermis, Journal of Investigative Dermatology, Jan. 2006 vol. 126 p. 49-60.*
Nicoloff et al., Journal of Investigative Dermatology, (Sep. 1, 2006), 11(1), pp. 16-29.*

* cited by examiner

*Primary Examiner* — Phyllis G. Spivack
(74) *Attorney, Agent, or Firm* — Jules E. Goldberg

(57) ABSTRACT

A method for the therapeutic treatment of psoriasis by the administration of an anti-psoriasis effective amount of Doxivir (CTC-96) is discloses.

4 Claims, No Drawings

METHOD FOR THE TREATMENT OF PSORIASIS

CROSS-REFERENCE TO RELATED APPLICATION

The application is based on U.S. Provisional Patent Application Ser. No. 60/867,679, filed Nov. 29, 2006 and International Application No. PCT/US2007/082227 filed Oct. 23, 2007 entitled "Method for the Treatment of Psoriasis", the priorities of which are hereby claimed.

BACKGROUND OF THE INVENTION

1. Field of the Invention

This invention pertains to the field of treatment of a subject infected with psoriasis.

2. Description of the Background

Psoriasis is a chronic disease of unclear pathogenesis, affecting skin and joints in ~2% of the population in developed countries. The disease causes significant morbidity. Some of its main characteristics are inflamed, scaly and frequently disfiguring skin lesions and arthritis of the joints in hands and feet. Typically, in the skin lesions, altered differentiation of epidermal keratinocytes accompanies keratinocyte hyperproliferation. Marked infiltrates of T-cells and neutrophils are characteristic of psoriatic skin and are directly involved in the inflammatory state of the affected tissue. In addition, a distinct increase in skin capillaries is a typical phenomenon in psoriasis[1].

Psoriatic arthritis appears in 10-30% of patients. In addition, the disease causes psoriatic skin lesions which are very itchy and which can result in severe scratching and disfigurement. The various manifestations of the disease make it more than a dermatologic nuisance as it interferes with many daily activities of the afflicted. As a consequence the disease also causes considerable psychological morbidity in many patients.

Current therapy for psoriasis includes anti-inflammatory agents such as steroids, specific anti-inflammatory cytokines and chemokines, and agents acting as anti-autoimmune therapies. While several of these therapies provide relief, many have undesirable side effects and none provide a cure.

SUMMARY OF THE INVENTION

It is proposed that novel therapies are necessary in order to achieve a sustained cure for the disease'. These must be aimed at defined targets in psoriatic lesions which comprise potential basic causes of the etiology of the disease, specific regulatory genes and some inflammatory activities. It would be ideal to find such therapies that are multi-targeted, thus simultaneously affecting various factors of the disease.

In view of the following discoveries of recent years on factors involved in the development of psoriasis and the mode of action of the drug, Doxovir (CTC-196), we have found that the drug may be used as a therapeutic agent for psoriasis. In particular, we have discovered that psoriasis may be therapeutically treated by administration of an anti-psoriasis effective amount of Doxovir (CTC-96). CTC-96, its structure and method of preparation is fully described in U.S. Pat. No. 5,756,491, the contents of which are fully incorporated herein by reference. The drug may be administered by any of the known medical methods, e.g., intramuscularly, intravenously, orally, nasally, transdermal application, etc.

DETAILED DESCRIPTION OF THE INVENTION

1. It was recently discovered that the transcription factor Zinc-finger protein Gli-similar (Glis1) is found only in psoriatic and not in the epidermis of healthy skin[2]. The expression of this protein is restricted to the suprabasal level of the psoriatic epidermis. Under experimental conditions, this transcription factor can be dramatically induced by phorbol myristate acetate (PMA) or interferon and is thus associated with hyperplasic, inflammatory epidermis[2]. The work of Nakanishi et al. suggests that Glis1 is involved in the regulation of the aberrant differentiation of psoriatic epidermis.

Glis 1 has a unique structure containing five Zinc-fingers of the cysteine 2: histidine 2 nature[3].

Doxovir (CTC-96) is an effective agent that selectively disrupts the structure and function of Zinc-fingers in which the Zinc is tetrahedrally coordinated to cysteines and histidines[4]. The mode of action of the drug involves displacement Zinc from the protein by the axial ligation of the drug's cobalt (III) complex to the nitrogen of the imidazole ring of the histidine residues. The zinc-finger bearing protein is thus inactivated[4].

We have discovered that Doxovir (CTC-96) will inactivate Glis1 in Psoriatic epidermis and as a result may selectively retard the abnormal proliferation and differentiation of psoriatic keratinocytes.

2. There have been several reports of the possibility that Human Papilloma Viruses (HPVs) are associated with at least certain manifestations of psoriasis (e.g. [5,6,7,8]). Papillomaviruses proliferate and affect the differentiation and proliferation of keratinocytes. The possible role of the virus (particularly HPV type 5) in the etiology or the maintenance of the abnormal differentiation of psoriatic human skin keratinocytes has thus been postulated.

JunB protein, a component of the ubiquitous transcription factor AP-1, regulates cell proliferation, differentiation, stress responses and cytokine expression in various tissues. It was found[9] that this protein is down regulated in keratinocytes of psoriatic lesions. This decrease may trigger chemokine/cytokine expression thus recruiting neutrophils and macrophages to the epidermis and thereby contributing to the phenotypic changes observed in psoriasis. Several types of HPV have been shown to reduce the expression of the JunB gene. It is hypothesized that HPV can, therefore, contribute to the inflammatory state of the keratinocytes in psoriatic lesions. In addition HPV interferes with keratinocyte differentiation and proliferation via the viral gene products E2, E6 and E7.

Doxovir has distinct anti-papillomavirus activity [10,11] The drug can reduce pathological manifestations of psoriasis that result from the activity of HPV in the psoriatic keratinocytes.

3. One of the main features of psoriasis is severe inflammation that is usually caused by over-production of reactive oxygen species by a variety of cell types, particularly neutrophils and macrophages which penetrate the psoriatic epidermis. The evidence for this is found in psoriatic patients[12] who often have decreased antioxidant levels in their erythrocytes and other tissues[13]. Thus steroids are widely used for therapy of the disease, not only to reduce auto-immune responses but also to modulate inflammatory damage caused by reactive oxygen species. The skin stage of the disease progresses to inflammatory psoriatic arthritis in 10-30% of patients. It has proven to have therapeutic activity for type II collagen-induced arthritis in mice[15].

It is, thus, suggested that Doxovir (CTC-96) by virtue of its superoxide scavenging activity may be capable of alleviating some of the inflammatory phenomena associated with psoriasis.

Doxovir (CTC-96) is particularly advantageous in that as a new anti-psoriatic drug for the following reasons:
1. It is efficacious against Papillomaviruses.
2. It may act effectively and specifically against a major psoriasis-associated transcription factor, Glis 1, which bears five Zinc-fingers and is not found in normal skin.
3. It may be effective in retarding or preventing psoriatic arthritis.
4. It has no adverse effects on intact skin when given as a topical ointment.
5. It is a unique molecule with distinct mode of action which differs from all existing psoriasis medications.

REFERENCES (1) Nickoloff, B. J.; Nestle, F. O. Recent Insights into the Immunopathogenesis of Psoriasis Provide New Therapeutic Opportunities. *J. Clin. Invest* 2004 113, 1664-1675.
(2) Nakanishi, G.; Kim, Y. S.; Nakajima, T.; Jetten, A. M. Regulatory Role for Kruppel-Like Zinc-Finger Protein Gli-Similar 1 (Glis1) in PMA-Treated and Psoriatic Epidermis. *J Invest Dermatol.* 2006, 126, 49-60.
(3) Kim, Y. S.; Nakanishi, G.; Lewandoski, M.; Jetten, A. M. GLIS3, a Novel Member of the GLIS Subfamily of Kruppel-Like Zinc Finger Proteins With Repressor and Activation Functions. *Nucleic Acids Res.* 2003, 31, 5513-5525.
(4) Louie, A. Y.; Meade, T. J. A Cobalt Complex That Selectively Disrupts the Structure and Function of Zinc Fingers. *Proc. Natl Acad. Sci. U.S.A.* 1998, 95, 6663-6668.
(5) Favre, M.; Orth, G.; Majewski, S.; Baloul, S.; Pura, A.; Jablonska, S. Psoriasis: A Possible Reservoir for Human Papillomavirus Type 5, the Virus Associated With Skin Carcinomas of Epidermodysplasia Verruciformis. *J Invest Dermatol.* 1998, 110, 311-317.
(6) Prignano, G.; Ferraro, C.; Mussi, A.; Stivali, F.; Trento, E.; Bordignon, V.; Crescimbeni, E.; Salvati, G.; Degener, A. M.; Ameglio, F. Prevalence of Human Papilloma Virus Type 5 DNA in Lesional and Non-Lesional Skin Scales of Italian Plaque-Type Psoriatic Patients: Association With Disease Severity. *Clin. Microbiol. Infect.* 2005, 11, 47-51.
(7) Simeone, P.; Teson, M.; Latini, A.; Carducci, M.; Venuti, A. Human Papillomavirus Type 5 in Primary Keratinocytes From Psoriatic Skin. *Exp. Dermatol.* 2005, 14, 824-829.
(8) Wolf, P.; Seidl, H.; Back, B.; Binder, B.; Hofler, G.; Quehenberger, F.; Hoffmann, C.; Kerl, H.; Stark, S.; Pfister, H. J.; Fuchs, P. G. Increased Prevalence of Human Papillomavirus in Hairs Plucked From Patients With Psoriasis Treated With Psoralen-UV-A. *Arch. Dermatol.* 2004, 140, 317-324.
(9) Zenz, R.; Eferl, R.; Kenner, L.; Florin, L.; Hummerich, L.; Mehic, D.; Scheuch, H.; Angel, P.; Tschachler, E.; Wagner, E. F. Psoriasis-Like Skin Disease and Arthritis Caused by Inducible Epidermal Deletion of Jun Proteins, *Nature* 2005, 437, 369-375.
(10) Bonnez, W.; Darrin, C.; Simpson, V. Virucidal Effect of CTC-96 Against Human Papilloma Virus (HPV) Type 11. 39th Interscience Conference on Antimicrobial Agents and Chemotherapy (ICAAC). ☐ ☐ ☐ 1999.
(11) Howett, M. K.; Neely, E.; Ward, M.; Winicov, I.; Fang, L.; Gershon, D. Inhibition of Bovine Papillomavirus Type 1 (BPV-1) Transformation and Human Papillomavirus Type 11 (HPV-11) Transcription by the Anti-Viral Agent, Doxovir. *Manuscript in preparation* 2003.
(12) Rocha-Pereira, P.; Santos-Silva, A.; Rebelo, I.; Figneiredo, A.; Quintanilha, A.; Teixeira, F. Erythrocyte Damage in Mild and Severe Psoriasis. *Br. J Dermatol.* 2004, 150, 232-244.
(13) Briganti, S.; Picardo, M. Antioxidant Activity, Lipid Peroxidation and Skin Diseases. What's New *J Eur. Acad. Dermatol. Venereol.* 2003 17, 663-669.
(14) Gershon, D.; Dori, Z. Anti-inflammatory and anti arthritic activity of metal compounds with superoxide scavenging activity. Technical report Redox Pharmaceutical Corp. 1986.
(15) Wooley, P. H.; Whalen, J. D. The Influence of Superoxide Scavenging Compound CTC 23 on Type II Collagen-Induced Arthritis in Mice. *Agents Actions* 1992, 35, 273-279.

What is claimed is:
1. A method for treating psoriasis in a subject in need of such treatment comprising administering an anti-psoriasis effective amount of Doxovir (CTC-96) to the subject.
2. The method of claim 1 wherein the CTC-96 is administered intramuscularly, intravenously, orally, nasally, or by transdermal application.
3. A method for inactivating zinc-finger protein Glis 1 in psoriatic epidermis comprising administering a zinc-finger protein Glis 1 inactivating effective amount of Doxovir (CTC-96) to the outbreak of psoriatic epidermis.
4. A method for retarding abnormal proliferation and differentiation of psoriatic keratinocytes comprising administering a psoriatic keratinocyte retarding effective amount of Doxovir (CTC-96) to the psoriatic keratinocytes.

* * * * *